United States Patent
Burt

(10) Patent No.: US 9,867,855 B2
(45) Date of Patent: *Jan. 16, 2018

(54) METHOD OF USING MITOTICALLY INACTIVATED STEM CELLS FOR DAMAGED TISSUE REPAIR

(71) Applicant: Richard Burt, Chicago, IL (US)

(72) Inventor: Richard Burt, Chicago, IL (US)

(*) Notice: Subject to any disclaimer, the term of this patent is extended or adjusted under 35 U.S.C. 154(b) by 231 days.

This patent is subject to a terminal disclaimer.

(21) Appl. No.: 14/697,281

(22) Filed: Apr. 27, 2015

(65) Prior Publication Data

US 2015/0328265 A1 Nov. 19, 2015

Related U.S. Application Data

(63) Continuation of application No. 12/354,522, filed on Jan. 15, 2009, now Pat. No. 9,017,658, which is a continuation-in-part of application No. PCT/US2007/073904, filed on Jul. 19, 2007.

(60) Provisional application No. 60/807,861, filed on Jul. 20, 2006.

(51) Int. Cl.
| | |
|---|---|
| *A01N 63/00* | (2006.01) |
| *A61K 35/545* | (2015.01) |
| *A61K 35/34* | (2015.01) |
| *A61K 41/00* | (2006.01) |
| *C12N 5/0735* | (2010.01) |
| *A61K 35/28* | (2015.01) |
| *C12N 5/0775* | (2010.01) |
| *C12N 5/077* | (2010.01) |
| *A61K 35/12* | (2015.01) |

(52) U.S. Cl.
CPC ............ *A61K 35/545* (2013.01); *A61K 35/34* (2013.01); *A61K 41/00* (2013.01); *C12N 5/0606* (2013.01); *A61K 35/12* (2013.01); *A61K 35/28* (2013.01); *C12N 5/0657* (2013.01); *C12N 5/0662* (2013.01); *C12N 2506/02* (2013.01)

(58) Field of Classification Search
USPC ................................ 424/93.2, 93.1; 435/325
See application file for complete search history.

(56) References Cited

U.S. PATENT DOCUMENTS

| | | | |
|---|---|---|---|
| 5,486,359 A | 1/1996 | Caplan | |
| 5,827,735 A | 10/1998 | Young | |
| 5,837,539 A | 11/1998 | Caplan | |
| 7,311,905 B2* | 12/2007 | Hariri | A61K 35/28 424/583 |
| 8,187,881 B2 | 5/2012 | Smith | |
| 9,017,658 B2* | 4/2015 | Burt | A61K 41/00 424/93.1 |
| 2002/0188963 A1 | 12/2002 | Loring | |
| 2004/0151704 A1 | 8/2004 | Berenson | |
| 2005/0106724 A1 | 5/2005 | Schierholz | |
| 2005/0255588 A1 | 11/2005 | Young | |
| 2007/0092494 A1 | 4/2007 | Higgins | |
| 2007/0274960 A1 | 11/2007 | Harman | |
| 2007/0292401 A1 | 12/2007 | Harmon | |
| 2008/0241113 A1 | 10/2008 | Walton | |
| 2011/0020291 A1 | 1/2011 | Banerjee | |
| 2011/0212062 A1 | 9/2011 | Falanga | |

FOREIGN PATENT DOCUMENTS

| | | |
|---|---|---|
| CN | 101449822 | 6/2009 |
| WO | 2004007697 | 1/2004 |
| WO | 2008011524 | 1/2008 |

OTHER PUBLICATIONS

Heng, Medical Hypotheses, 2005, vol. 6-4, p. 1085-1088.*
Brown, Kristy J., et al., "Advances in the Proteomic Investigation of the Cell Secretome." Expert Rev Proteomics, Jun. 2012, vol. 9, No. 3, pp. 337-345.
Choi, Dong-Sic, et al., "Proteomics of Extracellular Vesicles: Exosomes and Ectosomes." Mass Spectrometry Reviews, 2015, vol. 34 pp. 474-490.
Chute, John P., et al., "Ex vivo culture rescues hematopoietic stem cells with long-term repopulating capacity following harvest from lethally irradiated mice." Experimental Hematology, vol. 32, 2004, pp. 308-317.
Colombian Patent Application No. 09-015685, Colombian Office Action, 2 pages.
Dai, Wangde, et al., "Myocardial Regeneration by Embryonic Stem Cell Transplantation: Present and Future Trends." Expert Review of Cardiovascular Therapy, vol. 4, No. 3, May 2006, pp. 375-383.
European Patent Application No. 07840442.3, Examination Communication, dated Aug. 29, 2011, 4 pages.
European Patent Application No. 07840442.3, Extended European Search Report, dated Mar. 24, 2010, 5 pages.
Fraidenraich, Diego, et al., "Rescue of Cardiac Defects in Id Knockout Embryos by Injection of Embryonic Stem Cells." Science, Oct. 8, 2004, vol. 306, pp. 247-252.
Hassink, Rutger J., et al., "Stem Cell Therapy for Ischemic Heart Disease." Trends in Molecular Medicine, Oct. 2003, vol. 9, pp. 436-441.
Heng, B.C., et al., "Utilizing Human Embryonic Stem Cells As 'Catalysts' for Biological Repair and Regeneration: Challenges and Possible Strategies." Clinical and Experimental Medicine, May 2005, vol. 5, No. 1, pp. 37-39.

(Continued)

*Primary Examiner* — Michael Wilson
(74) *Attorney, Agent, or Firm* — Fitch Even Tabin & Flannery LLP

(57) ABSTRACT

The present invention is directed to the use of mitotically and/or lethally inactivated stem cells for the repair of damaged organs and/or tissues. Stem cells are mitotically and/or lethally inactivated and transplanted into damaged tissue. Any form of ex vivo inactivation of stem cells may be used such that the stem cells cannot undergo mitosis or cell division before in vivo application. Mitotically and/or lethally inactivated stem may be used to ameliorate numerous disease, injury, traumatic, ischemic, aging, and/or degenerative conditions in different types of organs and/or tissues.

6 Claims, 12 Drawing Sheets

(56) References Cited

OTHER PUBLICATIONS

Heng, Boon Chin, et al., "Potential Benefits of Co-transplanting Autologous Adult Stem Cells Together With Human Embryonic Stem Cells or Their Differentiated Derivatives." Annals of Clincal and Laboratory Science, vol. 35, No. 1, Jan. 2005, pp. 3-6.
Heng, Boon Chin, et al., "Transplanted Human Embryonic Stem Cells as Biological 'Catalysts' for Tissue Repair and Regeneration." Medical Hypotheses, vol. 64, No. 6, 2005 pp. 1085-1088.
Hodgson, Denice M., et al., "Stable Benefit of Embryonic Stem Cell Therapy in Myocardial Infarction." Am. J. Physiol. Heart Circ. Physiol., 2004, 287 (2), H471-H479.
International Application No. PCT/US2007/073904, International Search Report and Written Opinion of the International Search Authority, dated Aug. 29, 2008, 6 pages.
International Application No. PCT/US2013/030850, International Search Report and Written Opinion of the International Search Authority, dated May 21, 2013, 8 pages.
Ke, Qingen, et al., "Embryonic Stem Cells Cultured in Biodegradable Scaffold Repair Infarcted Myocardium in Mice." Acta Physiologica Sinica, 2005, 57 (6), pp. 673-681.
Lee, Jong-Kuen, et al., "Exosomes Derived from Mesenchymal Stem Cells Suppress Angiogenesis by Down-Regulating VEGF Expression in Breast Cancer Cells." PLos ONE, Dec. 2013, vol. 8, issue 12, pp. 1-11.
Schey, Kevin L., et al., "Proteomics Characterization of Exosome Cargo." Methods, Mar. 2015, <http://doi.org/10.1016/j.ymeth.2015.03.018>, pp. 1-8.
Singapore Patent Application No. 200900053-0, Search and Examination Report, Jun. 18, 2010, 7 pages.
Tauro, Bow J., et al., "Two Distinct Populations of Exosomes Are Released from LIM1863 Colon Carcinoma Cell-Derived Organoids." Molecular & Cellular Proteomics, 12.3, pp. 587-597.
Trounson, Alan. "Human Embryonic Stem Cells: Mother of All Cell and Tissue Types." Reproductive Biomedicine Online, Reproductive Healthcare Ltd, Cambridge, vol. 4, No. 1, Jan. 1, 2002, pp. 58-63.
Watson, G.E., et al., "Long-term in Vivo Transmission of Alpha-particle-induced Chromosomal Instability in Murine Haemopoietic Cells." International Journal of Radiation Biology, vol. 69, No. 2, 1996, pp. 175-182.

* cited by examiner

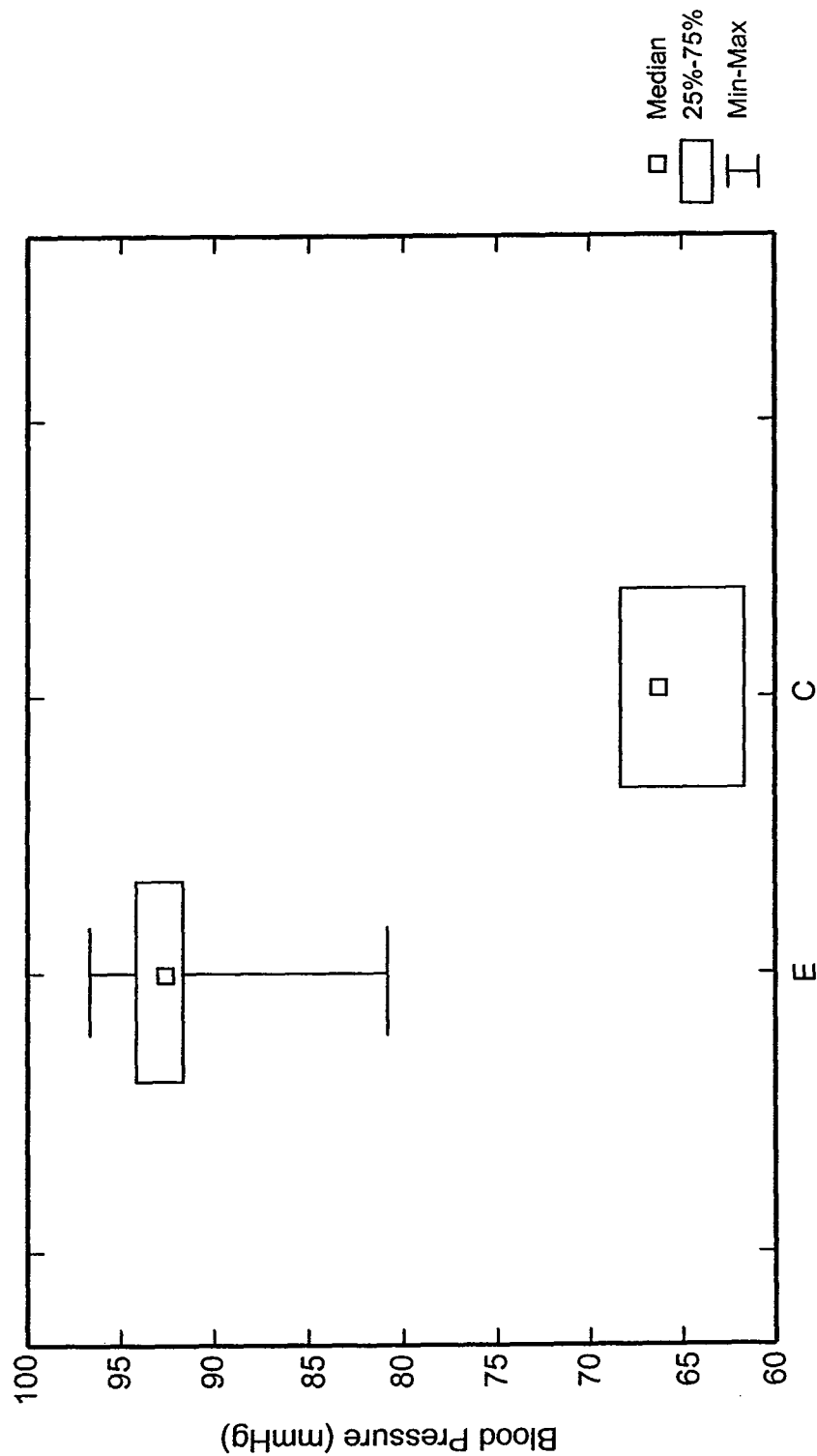

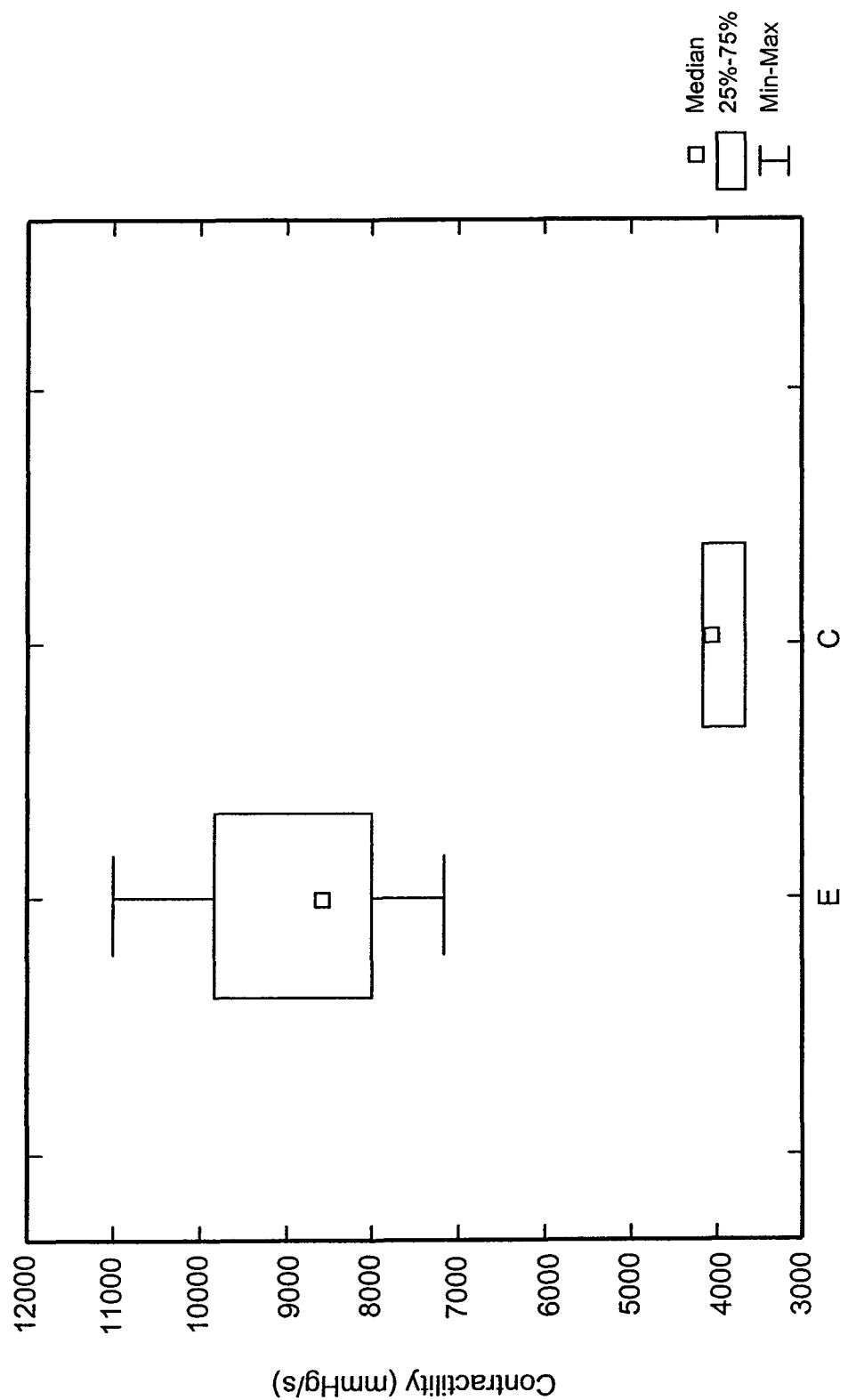

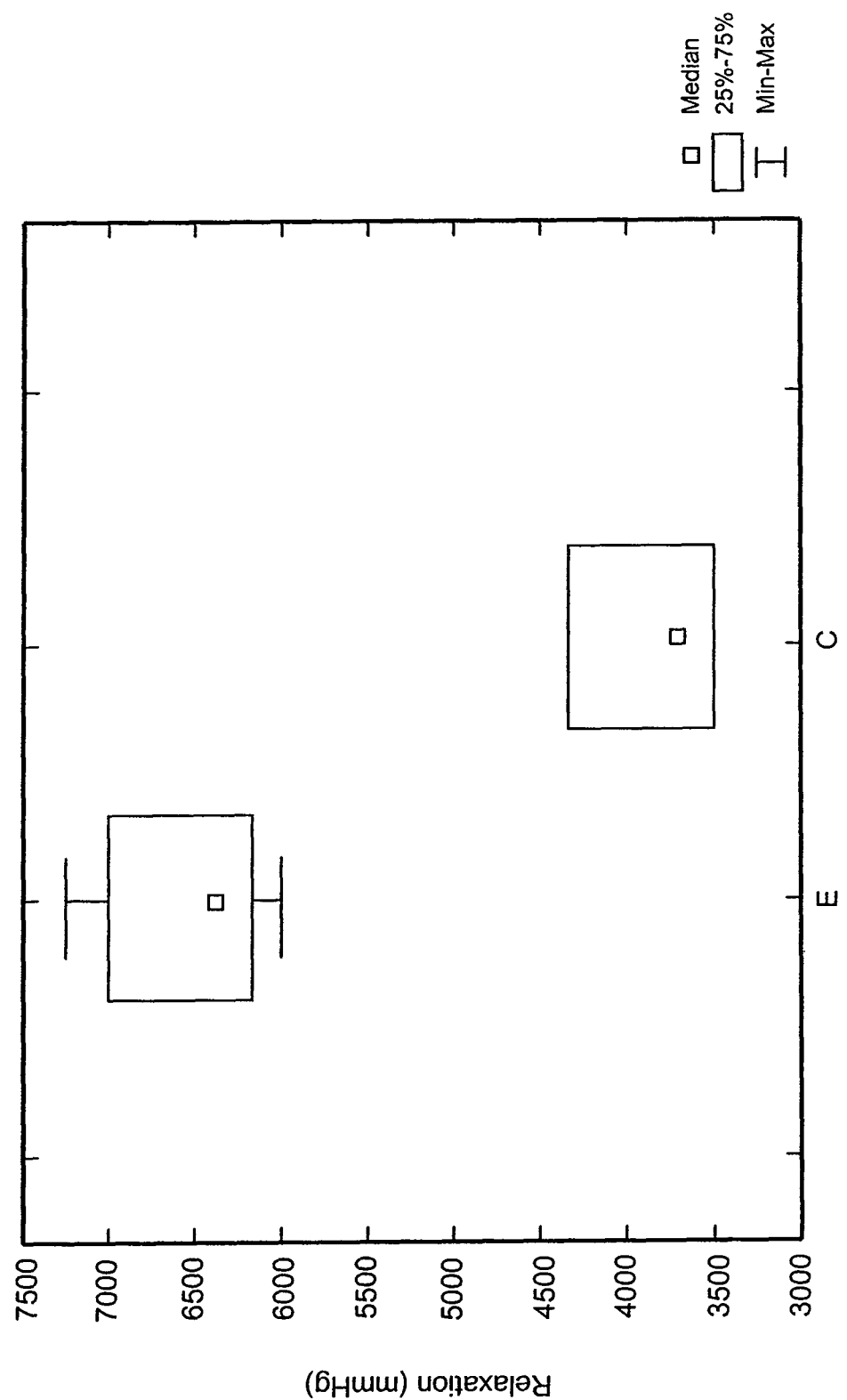

METHOD OF USING MITOTICALLY INACTIVATED STEM CELLS FOR DAMAGED TISSUE REPAIR

CROSS-REFERENCE TO RELATED APPLICATIONS

This application is a continuation application of U.S. application Ser. No. 12/354,522, filed Jan. 15, 2009, which is a continuation-in-part application of PCT/US2007/073904, filed Jul. 19, 2007, which claims the benefit of U.S. provisional application No. 60/807,861, filed Jul. 20, 2006, all of which are incorporated herein by reference in their entireties.

FIELD

The present invention is directed to the use of mitotically and/or lethally inactivated stem cells for the repair of damaged organs and/or tissues. Any form of ex vivo inactivation of stem cells may be used such that the stem cells cannot undergo unwanted mitosis or cell division before or after in vivo application. Mitotically and/or lethally inactivated stem may be used to ameliorate numerous disease, injury, and/or degenerative conditions in different types of organs and/or tissues.

BACKGROUND OF THE INVENTION

Stem cells, especially ESC due to pleuripotency, are being investigated to repair or rejuvenate tissue. However ESC, due to their pleuripotential (also spelled pluripotent) behavior, when injected in vivo form teratomas, a dysregulated, cancerous tumor growth. Teratomas are composed of cells from all three embryonic germ layers: mesoderm, endoderm, and ectoderm.

To circumvent generation of teratomas, ESC presently used in transplantation must be differentiated ex vivo into lineage committed adult stem cell phenotypes and or fully differentiated cells. This process is time consuming, requires maintenance of Good Manufacturing Procedures (GMP) over an extended period of time, and a method to purify the final product to ensure there is no contamination from residual pleuripotent ESC, and a method to ensure desired cell identity and lot to lot equivalency. ESC-derived cells must be grown ex vivo and maintained in feeder free and defined-media conditions to meet GMP guidelines.

Recent advances in cell culture technology have met GMP requirements for maintenance and expansion of undifferentiated ESC. However, in order to avoid teratoma formation, ESC must undergo costly and labor intensive differentiation into a mature somatic cell prior to in vivo application. In addition, these somatic cells must undergo purification or selection to avoid contamination with residual teratoma forming ESC or other undifferentiated or differentiated contaminating cells.

Further advances in ESC technologies have been restrained due to governmental restrictions and ethical issues surrounding the use of human ESC. Of concern to many is the use of human ESC in medical procedures.

Notwithstanding the ethical issues surrounding ESC, patients who have received transplanted ESC produced by current methods may require lifetime immune suppression to prevent ESC derived somatic cell rejection. Immune suppression may be accomplished by the use of immunosuppressants. Immunosuppressants are a class of drugs capable of inhibiting the body's immune system. Many of the agents included in this category are also cytotoxic (cell poisons) and are used in the treatment of cancer. Cytotoxic agents used as immunosuppressants include antimetabolites (azathioprine), alkylating agents (cyclophosphamide), and folic-acid antagonists (methotrexate or 6-MP). Other immunosuppressants include mycophenolate (CellCept) and cyclosporin. These drugs may be used in ESC transplant patients to decrease the body's own natural defense to foreign bodies (such as the transplanted ESC) and thereby, attempt to prevent the ESC rejection by the body.

Suppression of the immune system may create a number of undesirable side effects in a patient such as stomach upset, nausea, vomiting, abdominal pain, mouth ulcers, darkened urine, pale stools, jaundice (yellowing of the skin or white portion of the eyes), unusual bleeding or bruising. A serious (and life threatening) side effect is reduced activity of bone marrow, which is monitored with regular blood tests. Occasionally, patients taking immunosuppressants will develop pancreatitis (inflammation of the pancreas) some months after starting these drugs.

Additionally, patients undergoing immunosuppression therapy are at a greater risk for various infections including bacterial infections, herpes infections (such as cold sores and shingles), cytomegalovirus, fungal infections, and *Pneumocystis carinii* (a lung infection). Because patients are at an increased risk for infection, they may be required to have routine assessments to check for any signs or symptoms of infection. To prevent illness, patients may be required to take anti-viral medications such as acyclovir, cytovene, and valacyclovir; anti-fungal medications such as fluconazole and voriconzaole; and antibiotics such as Bactrim.

Patients receiving immunosuppressant therapy will likely experience substantial changes in daily routine. Patients must be vigilant in avoiding persons and activities posing a risk of infection.

Patients may need to restrict the number of individuals with whom they come in contact with on any given day and avoid crowded, enclosed areas. Patients must avoid contact with friends and family who have been sick including school-aged children. If a member of the patient's immediate family is ill, the patient may be required to stay in another room or stay in a hotel until the family member is no longer sick. Patients must also avoid contact with babies and children who have been recently vaccinated with the live-virus oral polio vaccine for at least eight weeks. Recipients of the vaccine can shed the virus in body excretions such as saliva and stool and infect an immunosuppressed individual. Patients may be required to avoid crowed places such as restaurants, churches or temples, retail stores, and public transportation.

Patients may also be restricted from performing or engaging in certain activities which have a high risk for infection. These activities may include changing a baby's diaper, interacting with pets, and gardening.

SUMMARY

The present invention is directed to a method for repairing damaged tissue by mitotically inactivating and/or lethally inactivating stems cells and transplanting the mitotically and/or lethally inactivated stem cells into the damaged tissue. The transplanted mitotically and/or lethally inactivated stem cells are effective for regeneration of damaged cells. Transplantation of the mitotically and/or lethally inactivated stem cells into the damaged tissue is not dependent on a permanent presence of the foreign stem cells in the recipient and the immune system of the recipient does not need to be suppressed to allow life-long engraftment. Furthermore for pleuripotent stem cells, mitotic inactivation prevents formation of teratomas. Every organ and or tissue in the body may be repaired using mitotically and/or lethally inactivated stem cells including but not limited to cardiac tissue, nerve tissue, muscle tissue, pancreatic tissue, skin tissue, and liver tissue. The method is effective for repairing these tissues in animals, including mammals, primates and humans.

Stem cells which may be utilized include pluripotent stem cells. Pluripotent stem cells include any stem cell independent of its in vivo source of origin such as but not limited to embryos (ESC), placenta, amniotic fluid, bone marrow, induced pleuripotent cells, or pleuripotent stem cells derived ex vivo from adult stem cell. A pluripotent stem cell is capable of differentiating into more than one germ line or tissue specific cell lineages.

Stem cells are mitotically and/or lethally inactivated by treating the stem cells with a method effective for inhibiting or preventing unlimited proliferation of stem cells. In this aspect, the embryonic stem cells are inactivated with irradiation, mitomycin C, phototherapy, or any agent that inhibits cell proliferation including but not limited to inhibitors of cellular components necessary for mitosis such as but not limited to protein synthesis, microtubule function, spindle check point unit, cell cycle specific kinases, cyclins, and or apoptotic inducing agents, as well as any means of genetic, protein, and or cell manipulation that will allow termination or prevention of unregulated or unlimited cell proliferation.

BRIEF DESCRIPTION OF THE DRAWINGS

FIG. 1a is a graphical representation of the results of Example 1 (discussed herein below) where median blood pressure (mmHg) in mice having irradiated ESC (IR-ESC) treated ischemic hearts is compared to median blood pressure (mmHg) in mice having ischemic hearts receiving no treatment.

FIG. 1b is a graphical representation of the results of Example 1 (discussed herein below) where median contractility (mmHg/s) in mice having IR-ESC treated ischemic hearts is compared to median contractility (mmHg/s) in mice having ischemic hearts receiving no treatment.

FIG. 1c is a graphical representation of the results of Example 1 (discussed herein below) where median relaxation (mmHg) in mice having IR-ESC treated ischemic hearts is compared to median relaxation (mmHg) in mice having ischemic hearts receiving no treatment.

DETAILED DESCRIPTION

Figure 2:
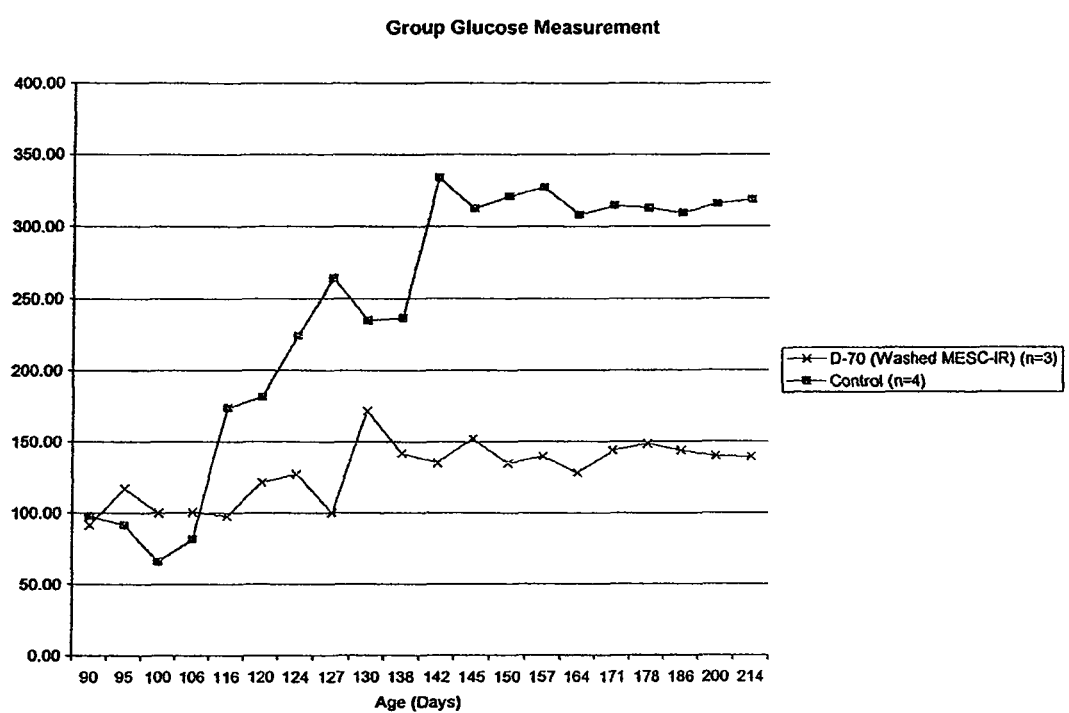
FIG. 2 demonstrates the effect of mitotically inactivated ESC treatment on diabetes.

The above and other problems addressed above are solved by the preferred embodiments discussed below. The following description is of the best mode presently contemplated for practicing the invention. This description is not to be taken in a limiting sense, but is made merely for the purpose of describing the general principles of the invention.

The invention advantageously eliminates the costly steps of stem differentiation and somatic cell purification because mitotically and/or lethally inactivated stem cells either allogeneic (from another person) tissue specific adult stem cells or plueripotent stem cells i.e. ESC (also allogenic) or allogeneic amniotic fluid derived pleuripotent stem cells (or pleuripotent stem cells from any source) can provide a transient in vivo chaperone assist to endogenous tissue without need of immune suppression or undesirable teratoma formation (ESC that are not mitotically inactivated form teratomas). As used herein, not forming teratomas means prevention of uncontrolled proliferation and its subsequent complications. Inactivated stem cells are not capable of undergoing unchecked cellular division and therefore do not form teratomas. Furthermore, because the stem cells chaperone effect is effective even if only present transiently, long-term (i.e life-long) immunosuppression in a patient is not necessarily a requirement of treatment with mitotically and/or lethally inactivated stem cells. Avoiding immunosuppression therapy drastically improves the patient's comfort and quality of life.

In another aspect of the invention, as demonstrated for the first time herein for embryonic stem cells, ESC produce a pronounced chaperone effect or in vivo cell-help-cell effect which mediates endogenous tissue regeneration. This chaperone or cell-help-cell effect is provided in vivo. ESC mediated chaperone effect is transient and rejection of the allogeneic ESC by host immune system does not diminish the effectiveness of the ESC.

In one embodiment, this chaperone effect can occur across xenogenic barriers allowing the substitution of animal ESC for human ESC for tissue regeneration which would mitigate ethical concerns and restraints on ESC therapies. In another embodiment, this chaperone effect could be obtained from pleuripotent stem cells derived from adult stem cells or from amniotic fluid or placenta or skin or other sources that would mitigate ethical concerns.

Stem Cells

Stem cells are undifferentiated cells that through replication have the capability of both self-renewal and differentiation into mature specialized cells. In broad terms, there are two types of stem cells, embryonic stem cells (ESC) and adult stem cells (ASC). Human ESC are traditionally isolated from a 50-to 150-cell, 4-to 5-day-old post-fertilization blastocyst. ESC generate every specialized cell in the human body; and while capable of indefinite ex vivo proliferation, exist only transiently in vivo—during embryogenesis. ASC are located in tissues throughout the body and function as a reservoir to replace damaged or aging cells. ASC are restricted in their differentiation to cell lineages of the organ system in which they are located. Stem cells are also referred to as toti-, pluri-, multi-, or unipotent. Totipotent stem cells arise from the morula and are capable of forming all cells essential for the body, including placental trophoblasts. In the next stage of embryonic development the morula becomes a blastocyst. Pluripotent stem cells traditionally arise from the blastocyst stage of development and give rise to every cell in the body, but not placental trophoblasts. Pleuripotent stem cells have also been recovered from amniotic fluid and may be found or generated from other sources such as placenta or from manipulation of ASC. ASC are multipotent stem cells in that their differentiation is limited to the tissue lineage or compartment in which they are located. Unipotent stem cells, also termed transient amplifying cells, are restricted in differentiation into a single specialized cell.

ESC have great promise and versatility but, compared to ASC, are currently difficult to tame due to their tendency to form all types of tissue within the body, i.e. a teratoma. In contrast, ASC normally behave well without formation of tumors, and follow traditional lineage-specific differentiation patterns, fulfilling their physiologic homologous function of replacing normal turnover, aging or damaged tissues.

Herein we demonstrate that ESC that are mitotically inactivated have a potent chaperone effect on endogenous tissue repair and do not form teratomas. While we demonstrate this effect for mitotically inactivated ESC, we maintain that mitotic inactivation of other pluripotent stem cells and even mitotically inactivated adult stem cells such as umbilical cord blood may convey, albeit with lesser efficacy, a similar effect without concern of uncheck proliferation of allogeneic cells in a genetically different recipient.

Pluripotent stem cells may be obtained originally from a number of sources including embryos, placenta, amniotic fluid, from manipulation of adult stem cells, and from various commercial sources that expanded the cells in culture.

Mitotic and/or Lethal Inactivation

Stem cells may be mitotically inactivated with any method effective for inhibiting unlimited proliferation of stem cells. Inhibiting unlimited proliferation means that stem cells do not present complications in vivo from uncontrolled proliferation.

Stem cells, such as ESC may be mitotically inactivated with radiation, mitomycin phototherapy, or any agent that inhibits cell proliferation including but not limited to inhibitors of cellular components necessary for mitosis such as but not limited to protein synthesis, microtubule function, spindle check point unit, cell cycle specific kinases, cyclins, and or apoptotic inducing agents. Stem cells may also be mitotically inactivated by any means of protein or genetic or cellular manipulation that will terminate or prevent unwanted proliferation and or differentiation. This approach applies to any form of ex vivo inactivation of stem cells so that the stem cells cannot undergo mitosis or cell division in vivo. We have shown that ESC provide a tissue repair chaperone effect after exposure to wide ranges of radiation doses of 10 to 40 Gy.

In another aspect, the stem cells may be lethally inactivated. Lethally inactivated means that the dose of radiation or apoptotic inducing agent is such that the ESC will not only stop dividing but die within hours, days, or weeks of injection.

Transplantation of Stem Cells

The invention disclosed herein utilizes mitotically inactivated and/or lethally inactivated stem cells for the repair of damaged organs and/or tissues. According to one embodiment, mitotically and/or lethally inactivated stem cells such as ESC are transplanted or injected into a site of aged or damaged tissue or intravenously or into surrounding fluid such as cerebrospinal fluid in a patient. This covers all routes of administration including but not limited to topical, intravenous, or direct injection into the tissue for delivering mitotically inactivated stem cells into the body in single or repeated intervals and in all doses.

Treatments

The methods described herein apply to all different types of organs and/or tissues for any type of injury, disease state, or natural degenerative state caused by aging. Virtually any organ can be repaired with mitotically and/or lethally inactivated stem cells such as ESC. For example, the types of organs and/or tissue that can be repaired by transplantation of mitotically inactivated stem cells include but are not limited to (1) heart or cardiac tissue after ischemic or traumatic injury, (2) brain or central nervous system (CNS) preservation after cerebral vascular accident or stroke, (3) oligodendrocyte repair in demyelinating CNS diseases such as multiple sclerosis, (4) aoxnal repair of degenerating CNS diseases such as Parkinsons, Huntingtons and Alzheimer's diseases, (5) rapid wound healing after trauma such as follows gun shot or explosive injuries, (6) repair of spinal cord injuries (SCI) for reinervation/remyelination, (7) prevention of tissue apoptosis and damage following radiation injury either from accidental exposure, following a terrorist attack, or for recovery from radiation induced injury used as medical therapy, (8) islet cell regeneration for type I and II diabetes, (9) lung tissue in patients with emphysema, (10) cartilage repair in degenerative or inflammatory joint diseases, (11) regeneration of ischemic renal epithelium after acute tubular injury (ATN), (12) regeneration of vascular supply to chronically or acutely ischemic tissue, and (13) repair of toxic and/or radiation induced tissue injury, and as a cosmetic or skin care product.

Although not wishing to be limited by theory, it is hypothesized that undifferentiated ESC provide a chaperone (cell-help-cell) effect by humoral or paracrine mediators and or cellular factors or factors mediated through cell contact that can mediate ASC or somatic cell proliferation, growth, and renewal which is required only transiently and can be provided by either lethally inactivated or mitotically inactivated ESC. This effect does not depend on immune acceptance of the ESC or on the establishment of a committed or differentiated cell progeny derived from the ESC. In this aspect, mitotically inactivated ESC may be used as an ex-vivo feeder layer for other cells. Mitotically inactivated ESC provide this cell-help-cell effect both in vivo and ex vivo. Therefore, this technology also applies to the use of mitotically inactivated ESC or induced pleuripotent stem cells, or other pleuripotent stem cells to help grow, expand, or increase the survival of other cells grown or manipulated ex vivo or in the laboratory or within a commercial or Good Manufacture Procedure (GMP) facility.

The method is advantageously simple and practical. It avoids differentiation of ESC which involves gene therapy or cytokine/media directed ex vivo differentiation and extensive purification of the ESC-derived somatic cell. The undifferentiated ESC can be directly used to augment organ specific regeneration without unwanted side effects of teratoma formation from non-mitotically inactivated ESC. This is a tremendous savings in time, effort, expense, and compliance with regulatory issues.

Furthermore, immune tolerance in patients is not required. ESC-derived or pluripotent stem cell-derived or adult allogeneic stem cell derived somatic cells are foreign and can be rejected by the recipient unless he/she receives life long immune suppression. The methods described herein do not require immune suppression. The paracrine or chaperone effect of the mitotically inactivated ESC is transient and immune mediated rejection or apoptosis of the ESC would be expected.

From an ethical standpoint, xenogeneic mitotically inactivated ESC in addition to human derived ESC are effective to treat disease and injury in mammals. Although human ESC may be superior for a given application, the use of mitotically inactivated ESC from another species avoids any ethical issue for a patient treatment arising from procurement and use of human ESC. Also from an ethical standpoint, mitotically inactivated pluripotent stem cells derived from non-embryonic sources such as but not limited to placenta or amniotic fluid or or skin or other tissues or derived from adult stem cells may be used with the same or similar albeit perhaps lesser effect.

Any type of mammal may be treated with mitotically and/or lethally inactivated stem cells. Examples of mammals that may be treated include, but are not limited to rodents, such as mice and rats, pigs, cats, dogs, and primates, including for example humans and chimpanzees. Since embryonic and pluripotent stem cells are a consistently conserved evolutionary theme, any type of mammal may likewise be a donor of stem cells, such as, for example, rodents such as mice and rats, pigs, cats, dogs, and primates, including, for example, humans and chimpanzees.

There are a wide range of applications for which the mitotically and/or lethally inactivated stem cells can be used. The applications are available for use in any organ system damaged by disease, trauma, ischemis, aging, degeneration, or exposure to noxious substances. In this aspect, mitotically and/or lethally inactivated stem cells may be used in cosmetic applications. Advantageously, many of the applications can be derived from a single off the shelf product. Since mitotically inactivated ESC are a universal product that can be used for any diseased or traumatized or ischemia organ independent of immunologic differences between individuals, they are a readily available off the shelf commercial product.

EXAMPLES

A better understanding of the present embodiment and of its many advantages may be clarified with the following example, given by way of illustration.

Example 1

Caridac Ischemia

Mouse irradiated (20 Gy to 50 Gy) ESC were injected into ischemic murine myocardium using coronary artery clamping as an ischemic/reperfusion model. Mice receiving irradiated ESC were compared to mice receiving non-irradiated ESC and mice receiving no ESC.

Mice with infarct receiving non-irradiated ESC and mitotically inactivated ESC showed a marked improvement in terms of cardiac relaxation and contractility in comparison to mice receiving no ESC.

Untreated ESC gave rise to malignant rapidly growing teratomas in several of the subject heart while no residual ESC could be found in the hearts or any other organ of animals receiving mitotically inactivated ESC.

The materials, methods, and results follow herein below:
Mice

Female 129X1/SvJ mice were purchased from the Jackson Laboratories (Jackson Lab, Bar Harbor, Me.) and housed in filtered-top cages under barrier conditions with easy access to water and food. All animal experiments were approved by the Institutional Animal Care and Use Committee of Northwestern University.
Embryonic Stem Cells Various animal ESC lines such as the 129/SvJX129/SV-CP male Fl hybrid 3.5-day mouse ($H-2^b$) blastocyst-derived embryonic stem cell lines or human ESWC line WA09 or human ESC line Cecol-14 or others may be utilized. Human ESC were obtained commercially (WiCell Research Madison, Wis.) as NIH approved cell line WA09. Human ESC line Cecol-14 was derived from Cecolfes, Bogota, Columbia ESC culture in maintenance culture may be performed in numerous published manners and are not unique for success of this approach. For mouse ESC, to maintain embryonic stem cells in an undifferentiated state, cells were cultured on gelatinized tissue culture dishes in high-glucose Dulbecco's modified Eagle's medium supplemented with 15% fetal bovine serum (FBS), 2 mM L-glutamine, 0,1mM β-mercaptoethanol, 1 × nonessential amino acids, 1 × sodium pyruvate and 1000 U/ml leukemia inhibitory factor (LIF) (Specialty Media, Phillipsburg, N.J.; StemCell Technologies, Vancouver, Canada). Mitomycin C-treated primary embryonic fibroblasts (StemCell Technologies) were used as a feeder layer for long-term culture of R1 ESC. Embryonic stem cells were cultured in gelatin-coated plastic dishes without PMEF for the two last passages before collection for the injection.
ESC Mitotic Inactivation and Analysis of Cell Proliferation ESC were grown under culture conditions as above to 70% confluence, then collected and irradiated with 30 Gy using Gammacell 40 irradiator one day prior the injection. Irradiated (20 to 50 Gy) and non-irradiated ESC were analyzed for proliferation rate using bromodeoxyuridine (BrdU) uptake. The cells were cultured in a total volume of 2mL in MESC media in the presence of LIF and 10 uL/mL of BrdU. 24 or 48 hours later, cells were harvested and processed with a BrdU Flow Kit (BD Pharmingen) according to the manufacturer's protocol. Cells were stained with FITC anti-BrdU and 7-amino-actinomycin (7-AAD). Flow cytometric data were acquired using an Epics XL flow cytometer and analyzed with CellQuest software.
Coronary Artery Ligation Anesthetized mouse was placed in a supine position with paws taped to the operating table. The tongue was slightly refracted. A150-W halogen light source (World Precision Instruments, Sarasota, Fla.) with two 24-in flexible fiber-optic arms allowed transillumination of the trachea just below the vocal cords to provide visualization of the trachea for endotracheal intubation. A catheter was inserted through the larynx and into the trachea. Ventilation was provided by a rodent ventilator. The chest was opened along the left side of the sternum cutting through the ribs to approximately midsternum. The chest walls were refracted by the use of 5-0 or 6-0 silk or monofilament suture. The left auricle was slightly refracted exposing the entire left main coronary artery system. Ligation proceeded with a 7-0 silk suture passed with a tapered needle underneath the left anterior descending branch of the left coronary artery 1-3 mm from tip of the normally positioned left auricle. A 1-mm section of PE-10 tubing was placed on top of vessel, and knot was tied on the top of the tubing to occlude the coronary artery. After occlusion for 60 minutes, reperfusion occurred by cutting the knot on top of the PE-10 tubing. Cells were injected into the ischemic myocardium at the border of the infarct site immediately before removing artery occlusion. The chest wall was then closed. The mouse was removed from the respirator, the endotracheal tube was withdrawn, and the mouse was kept warm by a heat pad and allowed 100% oxygen via nasal cone under intensive care for up to 24 hours. Functional studies and immunohistochemistry were done 30 days after coronary artery ligation.
Hemodynamics Measurement and Determination of Infarct Size Mice were anaesthetized. A high-fidelity transducer tipped pressure-volume catheter (SPR 839, Millar Instruments, Houston, Tex., USA) was zeroed in 37° C. saline. The right carotid artery was isolated, and two ties were gently pulled back, using hemostats, to block blood flow from the vessel. When pulsatile flow was no longer visible, a small cut was made just below the distal tie, and the catheter was placed inside the carotid artery, and secured in place. The transducer was advanced into the heart, where its position was confirmed by the rapid deflection of the diastolic pressure wave without any change in systolic pressure. Mice were allowed to stabilize for 30 min. After stabilization, 30 s of data were collected. At the end of data collection, the catheter was removed from the heart for measurement of arterial pressure, in order to verify that the valves were not damaged. The catheter was then removed from the mouse. Signals were digitized by use of a data translation series analog digital converter and then stored and analyzed on a Millar PVAN data acquisition and analysis system. Values derived from pressure traces were averaged no less than 20 bears. After ventricular function assessment, hearts were collected and fixed in 10% paraformaldheide. All hearts were cut into 4 blocks and were paraffin-embedded with flat side down. Serial sections of heart were cut at 5 µm thickness with a microtome.

Histology

Infarct size was assessed by H&E staining Infarct area was determined by planimetry using image analyzing software (NIH image). All sections of the 4 blocks of each heart were assessed. The infarct size was expressed as the average percentage of the left ventricle on the 4 blocks of each heart. H&E stained slides were used as well to analyze morphology of cardiomyocytes, the presence or absence of infiltration, and/or tumor growth within myocardium.

FISH Analysis

Single-label (whole Y-chromosome) FISH analysis was performed according to the manufacturer's protocol (Cambio Ltd, Cambridge, UK). Serial sections from paraffin-embedded whole heart block were cut (4 µm thickness) and prepared for procedure using tissue microarray (TMA). TMA permitted the combination of all tissue specimens including positive and negative controls on one slide. Tissue sections on coated slides were dewaxed, rehydrated, treated with sodium thiocyanate solution and pepsin, fixed and dehydrated. After air drying, 15-20 µl of denatured nucleotide probe was added to each slide, covered by coverslip and sealed. After overnight hybridization at 37 C, the coverslip was removed and serial washings were performed. Nuclei were counterstained with DAPI. Slides were examined by fluorescent microscope (Olympus BX-41) with an appropriate filter system.

Results

Actual values of contractility between mice with infarct receiving non-irradiated ESC (Non-irradiated ESC-N), mice that received mitotically inactivated ESC (Irradiated ESC-I), and mice getting infarct with no ESC injected (control-C) are shown in table 1.

TABLE 1

| Group | BP (mmHg) | Contractility (mmHg/s) | Relaxation (mmHg) |
|---|---|---|---|
| 1 | N | 92 | 8502 | 6079 |
| 2 | N | 95 | 8934 | 6400 |
| 3 | N | 90 | 7875 | 6008 |
| 4 | N | 92 | 9593 | 6384 |
| 5 | I | 91 | 10079 | 6996 |
| 6 | I | 82 | 7076 | 6408 |
| 7 | I | 94 | 7388 | 6204 |
| 8 | I | 92 | 7906 | 7059 |
| 9 | I | 96 | 10753 | 7162 |
| 10 | C | 62 | 3780 | 3553 |
| 11 | C | 66 | 4270 | 3710 |
| 12 | C | 68 | 4367 | 4230 |

Analysis of mean and median contractility between mice with infarct receiving non-irradiated ESC (Non-irradiated ESC-N), mice that received mitotically inactivated ESC (Irradiated ESC-I), and mice getting infarct with no ESC injected (control-C) are shown in table 2. Of importance there is no difference between irradiated and non-irradiated ESC in terms cardiac relaxation and contractility but there is marked improvement in both when compared to mice receiving no ESC.

TABLE 2

| Group | # | BP Mean ± SD | BP Median (Min; Max) | Contractility Mean ± SD | Contractility Median (Min; Max) | Relaxation Mean ± SD | Relaxation Median (Min; Max) |
|---|---|---|---|---|---|---|---|
| N | 4 | 92.3 ± 2.1 | 92 (90; 95) | 8712.3 ± 701.5 | 8718 (7875; 9538) | 6217.8 ± 203.4 | 6231.5 (6008; 6400) |
| I | 5 | 91 ± 5.4 | 92 (82; 96) | 8638.6 ± 1667.0 | 7906 (7067; 10753) | 6765.8 ± 429.9 | 6996 (6204; 7162) |
| C | 3 | 65.3 ± 3.1 | 66 (62; 68) | 4139 ± 314.7 | 4270 (3780; 4367) | 3831 ± 354.3 | 3710 (3553; 4230) |

TABLE 3

| Mann-Whitney U Test (Sheet1 in heart-ESC1) By variable group1 Marked tests are significant at $p < .05000$ | Mann-Whitney U Test (Sheet1 in heart-ESC1) By variable group1 Marked tests are significant at $p < .05000$ Rank Sum | Mann-Whitney U Test (Sheet1 in heart-ESC1) By variable group1 Marked tests are significant at $p < .05000$ Rank Sum | Mann-Whitney U Test (Sheet1 in heart-ESC1) By variable group1 Marked tests are significant at $p < .05000$ U | Mann-Whitney U Test (Sheet1 in heart-ESC1) By variable group1 Marked tests are significant at $p < .05000$ Z | Mann-Whitney U Test (Sheet1 in heart-ESC1) By variable group1 Marked tests are significant at $p < .05000$ p-level | Mann-Whitney U Test (Sheet1 in heart-ESC1) By variable group1 Marked tests are significant at $p < .05000$ Z |
|---|---|---|---|---|---|---|
| Blood Pressure (mmHg) | 72.00000 | 6.000000 | 0.00 | 2.496151 | 0.012555 | 2.513792 |
| Contractility (mmHg/s) | 72.00000 | 6.000000 | 0.00 | 2.496151 | 0.012555 | 2.496151 |
| Relaxation (mmHg) | 72.00000 | 6.000000 | 0.00 | 2.496151 | 0.012555 | 2.496151 |

TABLE 3-continued

| | Mann-Whitney U Test (Sheet1 in heart-ESC1) By variable group1 Marked tests are significant at p < .05000 | Mann-Whitney U Test (Sheet1 in heart-ESC1) By variable group1 Marked tests are significant at p < .05000 p-level | Mann-Whitney U Test (Sheet1 in heart-ESC1) By variable group1 Marked tests are significant at p < .05000 Valid N | Mann-Whitney U Test (Sheet1 in heart-ESC1) By variable group1 Marked tests are significant at p < .05000 Valid N | Mann Whitney U Test (Sheet1 in heart-ESC1) By variable group1 Marked tests are significant at p < .05000 2*1sided |
|---|---|---|---|---|---|
| Blood Pressure (mmHg) | | 0.011945 | 9 | 3 | 0.009091 |
| Contractility (mmHg/s) | | 0.012555 | 9 | 3 | 0.009091 |
| Relaxation (mmHg) | | 0.012555 | 9 | 3 | 0.009091 |

Conclusion

Mice with infarct receiving non-irradiated ESC and mitotically inactivated ESC showed a marked improvement in terms of cardiac relaxation and contractility in comparison to mice receiving no ESC. Untreated ESC gave rise to malignant rapidly growing teratomas in several of the subjects heart while no residual ESC could be found in the hearts or any other organ of animals receiving mitotically inactivated ESC.

Example 2

Diabetes

Both type I and Type II diabetes are due to insufficient insulin for body requirements. In type I diabetes, beta islet cell loss is relatively rapid and profound with loss of insulin production. Non-obese diabetic mice develop clinical diabetes about 90 to 100 days of age. This process is due to immune-mediated destruction of insulin producing islet cells. We had previously demonstrated that mitotically inactivated ESC could repair ischemic injury induced dysfunction of myocardium. We next determined whether mitotically inactivated ESC could repair or prevent diabetes in NOD mice. The materials methods and results follow herein below Mice Six week old NOD/Ltj mice were obtained from Jackson laboratory.

Embryonic Stem Cells

Various animal blastocyst-derived embryonic stem cell lines may be utilized to maintain mouse embryonic stem cells in an undifferentiated state, cells were cultured on gelatinized tissue culture dishes in high-glucose Dulbecco's modified Eagle's medium supplemented with 15% fetal bovine serum (FBS), 2 mM L-glutamine, 0.1 mM β-mercaptoethanol, 1× nonessential amino acids, 1× sodium pyruvate and 1000 U/ml leukemia inhibitory factor (LIF) (Specialty Media, Phillipsburg, N.J.; StemCell Technologies, Vancouver, Canada). Mitomycin C-treated primary embryonic fibroblasts (StemCell Technologies) were used as a feeder layer for long-term culture of R1 ESC. Embryonic stem cells were cultured in gelatin-coated plastic dishes without PMEF for the two last passages before collection for the injection.

ESC Mitotic Inactivation and Analysis of Cell Proliferation

ESC were grown under culture conditions as above to 70% confluence, then collected and irradiated with 30 Gy using Gammacell 40 irradiator one day prior the injection. Irradiated (20 to 30 Gy) and non-irradiated ESC were analyzed for proliferation rate using bromodeoxyuridine (BrdU) uptake. The cells were cultured in a total volume of 2 mL in MESC media in the presence of LIF and 10 uL/mL of BrdU. 24 or 48 hours later, cells were harvested and processed with a BrdU Flow Kit (BD Pharmingen) according to the manufacturer's protocol. Cells were stained with FITC anti-BrdU and 7-amino-actinomycin (7-AAD). Flow cytometric data were acquired using an Epics XL flow cytometer and analyzed with CellQuest software.

ESC Transplantation

Mice were divided into control and mitotically inactivated ESC treated groups. Control mice received no intervention. Treated mice received intravenous (tail vein) injection of 5 million ESC that had been irradiated with 30 gray and washed with PBS three times. The irradiated ESC were injected in 200 ul PBS on day 70 of the animals life.

Blood Glucose Monitoring

A drop of peripheral blood was obtained by puncturing one lateral tail vein with a 25 G needle. Blood glucose was measured using OneTouch Strip and Accu-Check Advantage Kit. Measurements were performed twice a week since the first injection. Glycemia above 300 mg/ml was consider hyperglycemic.

Results

All NOD mice treated with irradiated ESC remained euglycemic without evidence of diabetes, while all control (untreated) mice developed diabetes, as demonstrated in FIG. 2.

No NOD mice treated with irradiated ESC developed clinical or histological evidence for teratomas. The chaperone (cell-help-cell) effect of mitotically inactivated ESC may be due to paracrine, cell fusion, growth factor, angiogenic or antiapoptotic effects as well as beneficial immune mediated effects.

Example 3

Lethal Radiation Injury

Figure 3:
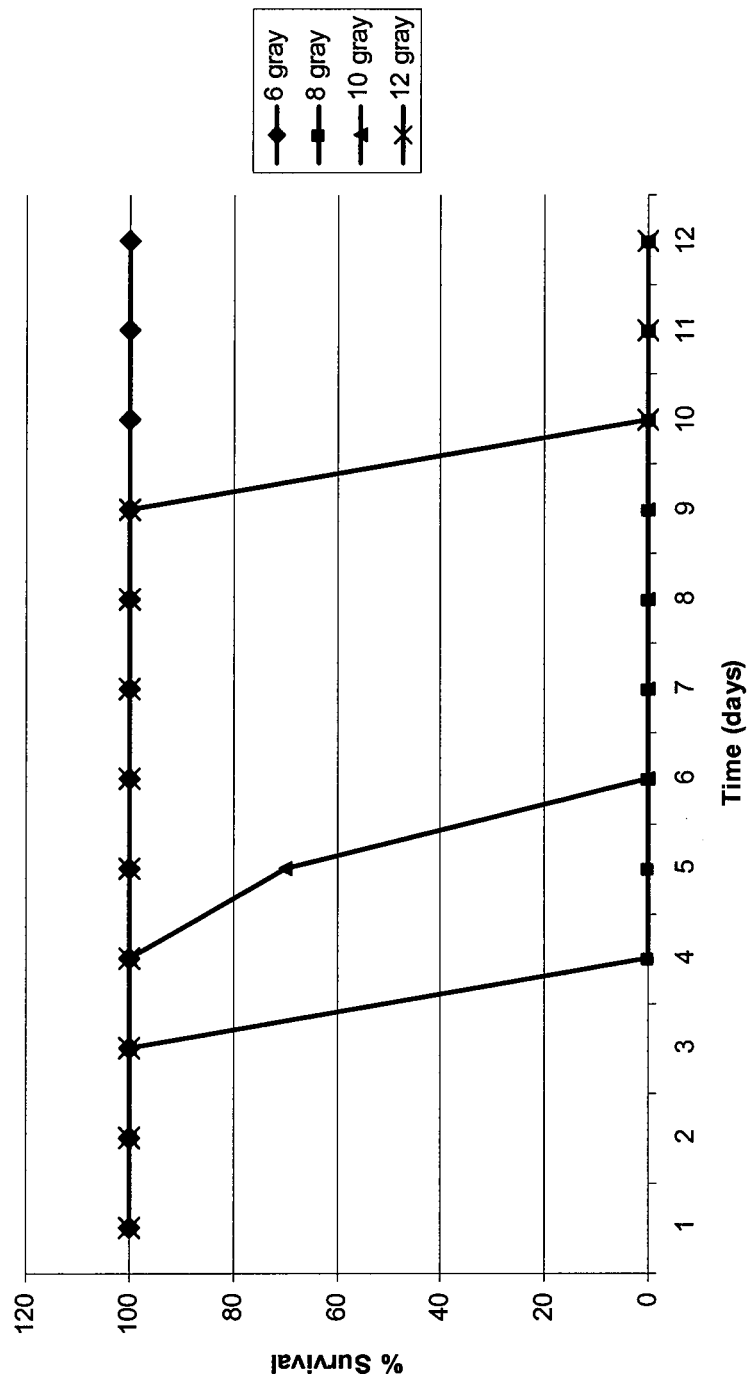
FIG. 3 shows % survival following different does of total body irradiation.

Lethal dose of total body irradiation—SJL/J mice survival was determined following different doses of total body irradiation (TBI) as shown in FIG. 3.

Figure 4:
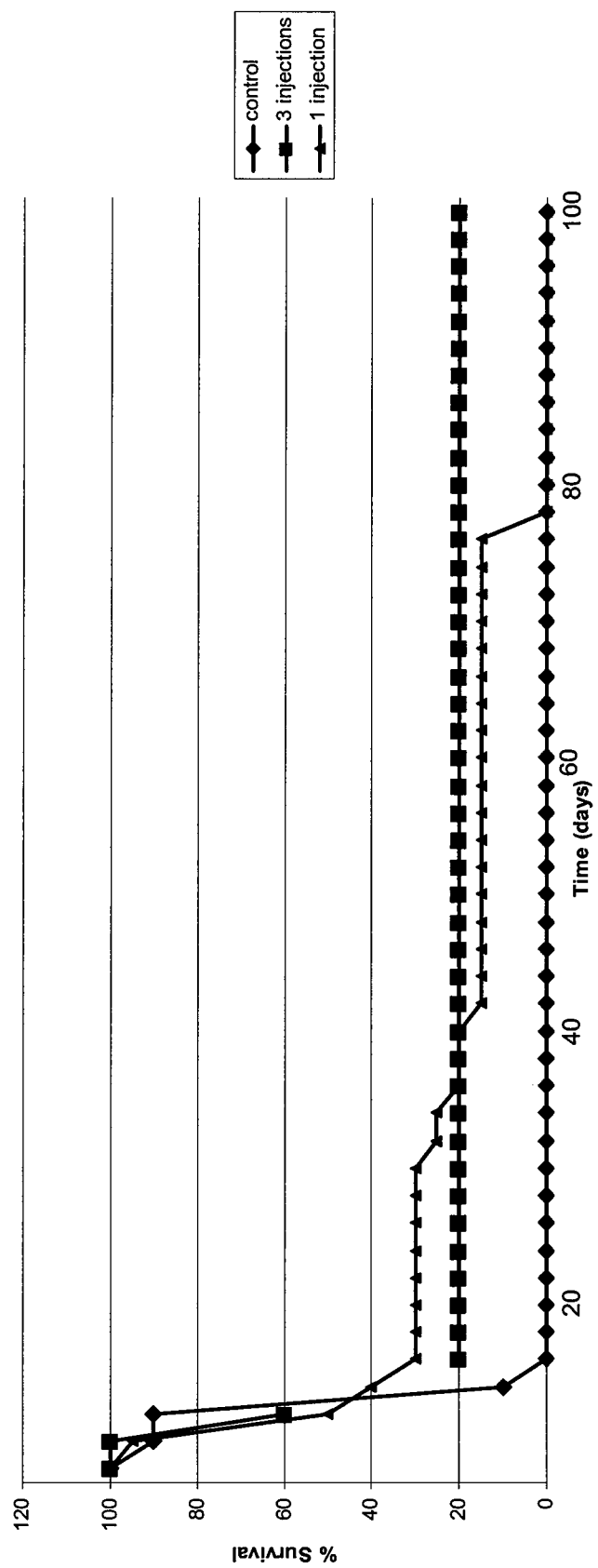
FIG. 4 shows a survival curve for total body irradiation (TBI) experiments in controls (exposed to TBI) compared to mammals exposed to TBI and then injected with mitotically inactivated ESC.

At 8 grays single dose TBI all mice died with 12 days. Next we irradiated mice with 8 gray TBI and while control mice received no further therapy, treated mice either received one injection one day after TBI or 3 injections on days 0, 2, and 4 after TBI. Irradiated washed ESC were injected either intravenous (tail vein or retro-orbital) at 5 million ESC per injection. Results are shown in FIG. 4.

All mice receiving 8 gray TBI alone died, only mice receiving mitotically inactivated ESC (treated with 30 Gy irradiation prior to injection) survived. Irradiated mice were female and injected mitotically inactivated ESC were male. There was no documentation of circulating y-chromosmes. The mitotically inactivated ESC provided a chaperone effect to endogenous hematopoiesis and there appeared to be a dose response effect with higher doses of mitotically inactivated cells injected over several days giving longer survival. No teratomas occurred, while injection of untreated ESC into irradiated mice resulted in teratoma formation at sites of injection in some mice.

Example 4

Comparison of ESC Versus IR-ESC on Treatment of Cardiac Disease

Materials and Methods
Mice

Female ICR mice (25~28 g) were purchased from the Harlan Sprague Dawley, Inc., Indianapolis, Ind., and housed in filtered-top cages under barrier conditions with free access to water and food. All animal experiments were approved by the Institutional Animal Care and Use Committee of Northwestern University.
Cell Culture The 129/SvJX129/SV-CP male F1 hybrid 3.5-day mouse (H-2b) blastocyst-derived embryonic stem cell line, R1 was maintained in embryonic stem cells in an undifferentiated state, cells were cultured on an embryonic fibroblast feeder layer inactivated with Mitomycin C (PMEF-N) (Millipore) in ESC medium composed of Knockout DMEM Invitrogen) supplemented with 15% ES cell qualified fetal bovine serum (Millipore), 2 mM L-glutamine (Hyclone), 0.1 mM β-mercaptoethanol (Sigma), 0.1 mM MEM nonessential amino acids (Hyclone), and 1000 U/ml leukemia inhibitory factor (LIF) (Millipore). Medium were changed daily and cell were split every other day.

PMEF-N cells were cultured on gelatin-coated culture plate in MEF medium composed of Knockout DMEM (Invitrogen) supplemented with 10% ES cell qualified fetal bovine serum (Millipore), 2 mM L-glutamine (Hyclone), 0.1 mM MEM nonessential amino acids (Hyclone) for at least overnight before plating of ES cells. Pure R1 embryonic stem cells (ESC) were cultured on gelatin-coated culture dishes without feeder layer for at least two passages before any experiments.
ESC Proliferation Assay Cell number was analyzed by measuring DNA content with the fluorescent dye Hoechst 33258 (Sigma, St. Louis, Mo.). Briefly, ESC were seeded in culture medium at $3 \times 10^3$ cells/well of a flat bottom 96 well tissue culture plate. After 48, 72, and 96 hours, medium was sucked off by aspiration and 100 µl ddH2O was added into each well. The plates were kept in −80° C. for at least 1hr and thawed before adding 100 µl of THE buffer (in total of 500 ml buffer, there were 10 ml 0.5M ph7.4 Tris, 1 ml 0.5M EDTA, 200 ml 5M NaCl, and 289 ml ddH$_2$O) with 0.2% Hoechst 33258 and well mixed. Plates were read at wavelength 355 nm/460 nm by 1420 multilabel counter (Wallac/Perkin Elmer, Bostin, Mass.).
ESC Viability Assay ESC were seeded in culture medium at $2 \times 10^3$ cells/well of a flat bottom 96 well tissue culture plate. After 48 and 72 hours, ATP content was measured in accordance with the protocol of the CellTiter-Glo™ luminescent cell viability assay (Promega, Madison, Wis.) kit. Briefly, 100 ul of assay reagent was added to the wells and mixed for 2 min at room temperature. After 10 min, intracellular ATP content was measured using a luminescence multilabel counter.
Adult Mouse Cardiomyocyte Isolation Adult mouse cardiomyocytes were isolated from female ICR mice by using the cardiomyocyte isolation kit (Cellutron) with Langendorf perfusion system. Cardiomyocytes were re-suspended in AS medium (Cellutron) and allowed to attach for 2 hours on laminin-coated 12-well plate at density $0.3 \times 10^5$ before the co-culture experiment. Cardiomyocytes represent 85-90% of total adherent cells.
Cardiomyocytes Co-Culture with Irradiated Embryonic Stem Cells (IR-ESC)

ESC were collected and irradiated at different dosage (20, 25, 30, 35 Gy) using Gammacell 40 irradiator one hour prior co-culture experiment. IR-ESC were washed and re-suspended in the condition medium which contain half AS medium and half ESC medium with LIF. Cardiomyocytes medium were replaced to condition medium 2 hours after seeded. IR-ESC were seeded at the density $0.3 \times 10^5$ into cell culture inserts (pore size 0.4 um; BD) and placed immediately into the respective wells with cardiomyocytes. The condition medium were changed daily during the co-culture assay. Non-co-cultured cardiomyocytes included as controls in this assay. After 48 hours of co-culture, the living cell numbers of cardiomyocytes were counted using a hemacytometer and trypan blue.
Mouse Myocardial infarction (MI) and IR-EMC transplantation ESC were collected and irradiated at dosage 25 Gy using Gammacell 40 irradiator one hour prior transplantation. $1 \times 10^6$ non-irradiated ESC and IR-ESC were washed and re-suspended in 10 ul Knockout DMEM medium without FBS respectively.

There are four different groups in this experiment. All groups of mice received myocardial infarction surgery before any treatment. Treatment groups received IR-ESC, non-irradiated ESC, and 10 ul medium respectively. Control group had surgery without any treatment.

Mice were anesthetized with a mixture of ketamine (100 mg/kg), xylazine (10mg/kg) and atropine (0.04 mg/kg) given intra-peritoneal. An anesthetized mouse was placed in a supine position with paws taped to the operating table. The tongue was slightly retracted. A150-W halogen light source (World Precision Instruments, Sarasota, Fla.) with two 24-in flexible fiber-optic arms allowed transillumination of the trachea just below the vocal cords to provide visualization of the trachea for endotracheal intubation. A catheter was inserted through the larynx and into the trachea. Ventilation was provided by a rodent ventilator. Left thoracotomy was done at the $4^{th}$ intercostals space. The chest walls were retracted by the use of 5-0 silk or monofilament suture. The left auricle was slightly retracted exposing the entire left main coronary artery system. Ligation proceeded with a 7-0 silk suture passed with a tapered needle underneath the left anterior descending branch of the left coronary artery <2 mm from tip of the normally positioned left auricle. A 1-mm section of PE-10 tubing was placed on top of vessel, and knot was tied on the top of the tubing to occlude the coronary artery. After occlusion for 60 minutes, reperfusion was restored by cutting the knot on top of the PE-10 tubing. Three intramyocardial injections of 10 µl of medium±$1 \times 10^6$ ES cells were injected into the infarction, border, and normal zones via a microsyringe. The chest wall was then closed. The mouse was removed from the respirator, the endotracheal tube was withdrawn, and the mouse was kept warm by a heat pad and allowed 100% oxygen via nasal cone under intensive care until full recovery. Functional studies, Bromodeoxyuridine, and FISH analysis were done 30 days after the surgeries.

Hemodynamics Measurements

Mice were anaesthetized. A high-fidelity transducer tipped pressure-volume catheter (SPR 839, Millar Instruments, Houston, Tex., USA) was zeroed in 37° C. saline. The right carotid artery was isolated, and two ties were gently pulled back, using hemostats, to block blood flow from the vessel. When pulsatile flow was no longer visible, a small cut was made just below the distal tie, and the catheter was placed inside the carotid artery, and secured in place. The transducer was advanced into the heart, where its position was confirmed by the rapid deflection of the diastolic pressure wave without any change in systolic pressure. Mice were allowed to stabilize for 30 min. After stabilization, 30 s of data were collected. At the end of data collection, the catheter was removed from the heart for measurement of arterial pressure, in order to verify that the valves were not damaged. The catheter was then removed from the mouse. Signals were digitized by use of a data translation series analog digital converter and then stored and analyzed on a Millar PVAN data acquisition and analysis system. Values derived from pressure traces were averaged no less than 20 bears.

FISH Analysis

Single-label (whole Y-chromosome) FISH analysis was performed according to the manufacturer's protocol (Cambio Ltd, Cambridge, UK). Serial sections from paraffin-embedded whole heart block were cut (4 µm thickness) and prepared for procedure using tissue microarray (TMA). TMA permitted the combination of all tissue specimens including positive and negative controls on one slide. Tissue sections on coated slides were dewaxed, rehydrated, treated with sodium thiocyanate solution and pepsin, fixed and dehydrated. After air drying, 15-20 µl of denatured nucleotide probe was added to each slide, covered by coverslip and sealed. After overnight hybridization at 37 C, the coverslip was removed and serial washings were performed. Nuclei were counterstained with DAPI. Slides were examined by fluorescent microscope (Olympus BX-41) with an appropriate filter system.

Bromodeoxyuridine Assay

One hour after the surgery, mice were administered with BrdU i.p. injection daily (75 mg/kg; Sigma) for 5 days. Mice hearts were harvested one month after surgery and fixed in 4% formaldehyde for immunohistochemistry study. The heart sections were embedded and cut into 5-um thick sections. The anti-BrdU In-Situ Detection Kit (BD Pharmagen) was used to target the BrdU-positive cells in the infarcted heart, according to the manufacturer's protocol. The number of stained cells was counted.

Statistical Analysis

Experiments were repeated a minimum of three times. All data are presented as either mean±SD or mean±S.E.M. All statistical comparisons between different groups were performed by Student's two-tailed t test and a P value of less than 0.05 was considered statistically significant.

Results

Intramyocardial injection of irradiated ESC improves cardiac function in myocardial infarction (MI) disease mice model without intra-cardiac teratomas formation. We hypothesize that inactivating mitotic ability of ESC with irradiation (IR-ESC) will prevent unregulated proliferation and in vivo teratoma formation from plueripotent ESC. We thus compared the effect of ESC versus IR-ESC on treatment of cardiac diseases. Six to eight week old ICR mice underwent ventilator assisted open thoracotomy and one hour ligation of the left anterior descending coronary artery. Prior to release of the ligated coronary artery and surgical closure, mice were divided into 2 control and 2 treatment groups. Control groups received either no injection or injection of supernatant from ESC cultures. Treatment groups underwent intra-myocardial injection of either ESC or IR-ESC that were washed and re-suspended in DMEM without FBS. All injections were performed under direct vision into myocardium at the border between healthy perfused and ischemic myocardium.

Figure 5:
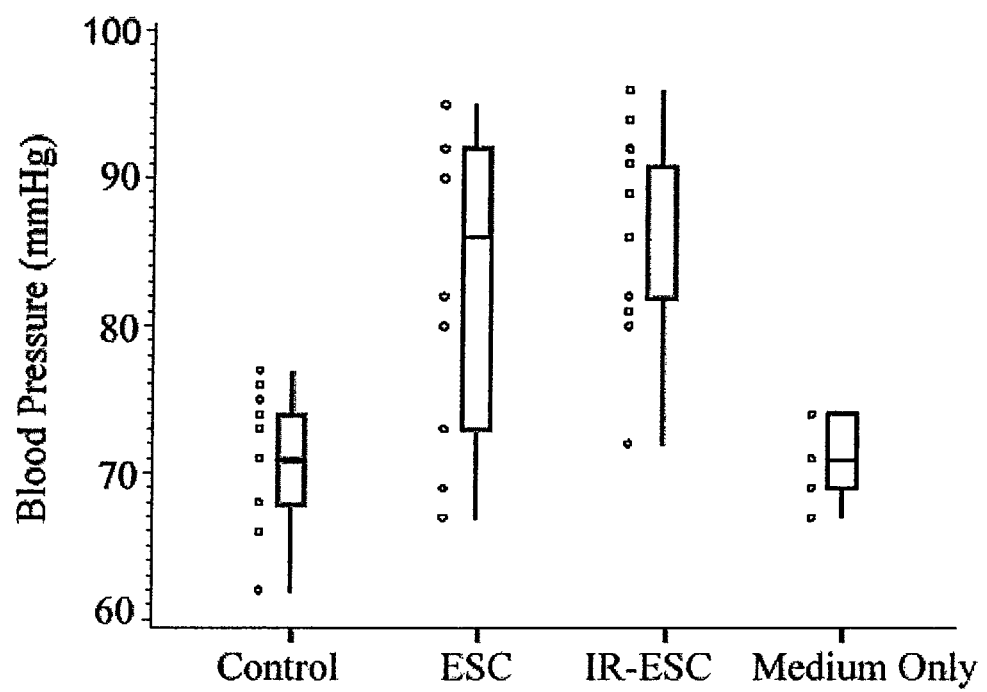
FIG. 5 illustrates post coronary artery ligation function.
Figure 6A:
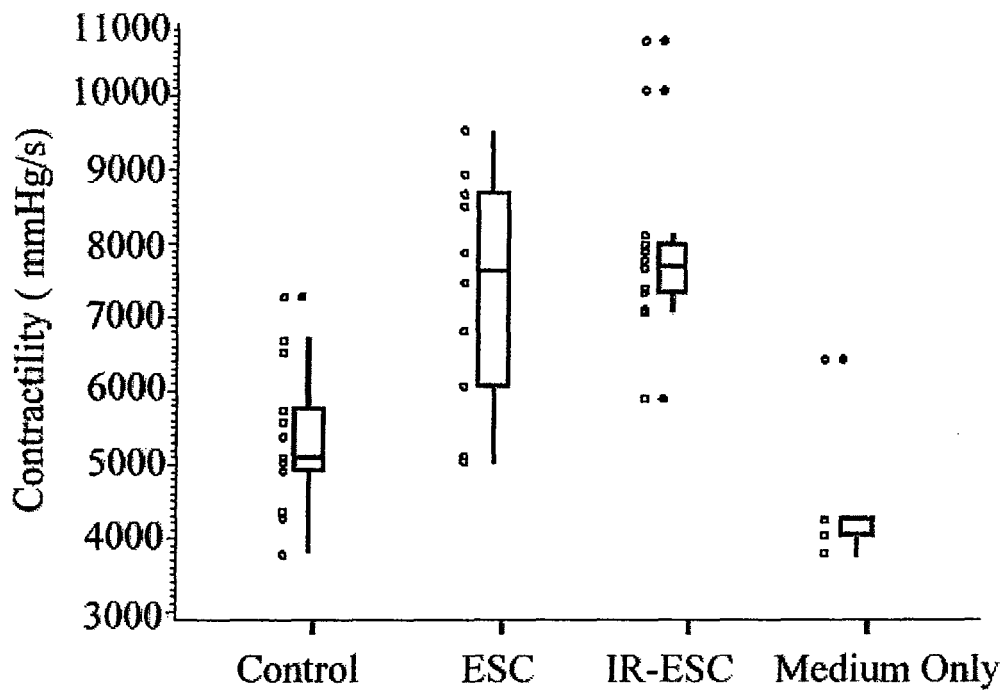
FIG. 6a and FIG. 6b describe values of cardiac function (blood pressure, contractility, and relaxation) between different treatment groups.
Figure 6B:
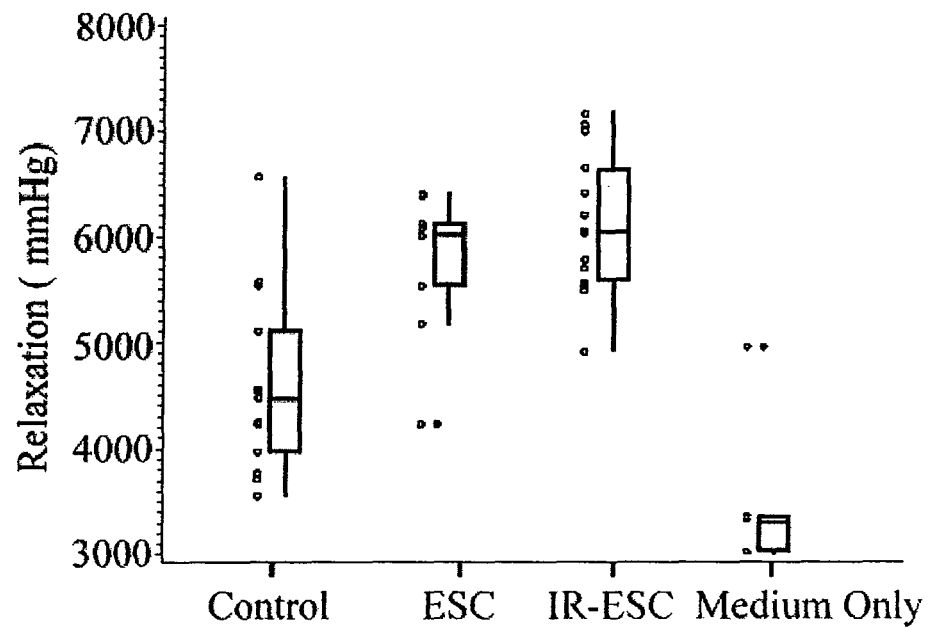

One month later, a high-fidelity transducer tipped pressure-volume catheter was introduced via the carotid artery into the left ventricle to monitor blood pressure, cardiac contractility, and cardiac relaxation. Mice receiving ESC had a significant improvement in cardiac indices compared to control mice that had coronary artery ligation or injection of supernatant media from ESC culture after coronary ligation (FIG. 5, FIG. 6A and FIG. 6B, and Table 4). In FIGS. 6A and 6B different treatment groups are depicted as box and whiskers plots. The line within the box represents the median ($50^{th}$ percentile). The length of each box shows the range of the central 50% of the value ($25^{th}$ and $75^{th}$ percentiles), and the whiskers indicate the $5^{th}$ and $95^{th}$ percentiles. Values outside the outer fences are plotted as dark circles.

Following injection of either ESC or IR-ESC, cardiac performance improved significantly (Table 4). One month after intra-myocardial injection of IR-ESC, systemic blood pressure, cardiac contractility and cardiac relaxation were improved ($p<0.01$) compared to controls. On autopsy, despite immune competent mice receiving HLA disparate ESC, two out of 8 mice treated with non-irradiated ESC had intra-cardiac teratomas. No mice treated with IR-ESC demonstrated teratomas in any organ system.

TABLE 4

|  | Control | ESC | IR-ESC | Medium Only |
|---|---|---|---|---|
| Blood Pressure (mmHg) | | | | |
| Mean ± S.E.M | 71.23 ± 1.19 | 83.2 ± 3.33 | 85.07 ± 1.75 | 71 ± 1.38 |
| P value (VS. Control) | | <0.01* | <0.01* | 0.915 |
| P value (VS. Medium Only) | 0.915 | <0.05** | <0.01* | |
| Contractility (mmHg/s) | | | | |
| Mean ± S.E.M | 5365.7 ± 278.0 | 7403.8 ± 503.8 | 7882.4 ± 324.5 | 4552.0 ± 477.4 |
| P value (VS. Control) | | <0.01* | <0.01* | 0.149 |
| P value (VS. Medium Only) | 0.149 | <0.01* | <0.01* | |

TABLE 4-continued

|  | Control | ESC | IR-ESC | Medium Only |
|---|---|---|---|---|
| Relaxation (mmHg) | | | | |
| Mean ± S.E.M | 4602.9 ± 243.0 | 5806.7 ± 210.9 | 6110.7 ± 180.3 | 4552.0 ± 477.4 |
| P value (VS. Control) | | <0.01* | <0.01* | 0.032 |
| P value (VS. Medium Only) | 0.032 | <0.01* | <0.01* | |

Cardiac function were tested 1 month after the myocardial infarction surgery and ESC transplantation.
*P < 0.01
**P < 0.05

Irradiated ESC Fail to Proliferate.

Figure 7A:
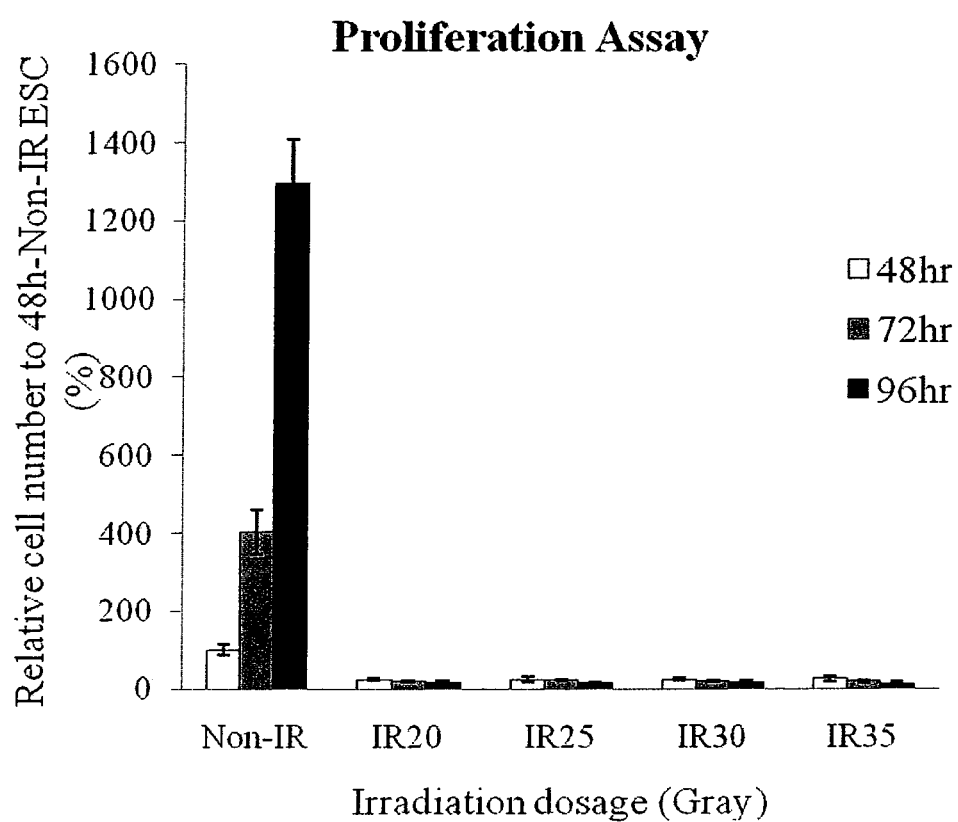
FIG. 7a and FIG. 7b describe proliferation ability of ESC treated with different dosage or irradiation and different duration of treatment.
Figure 7B:
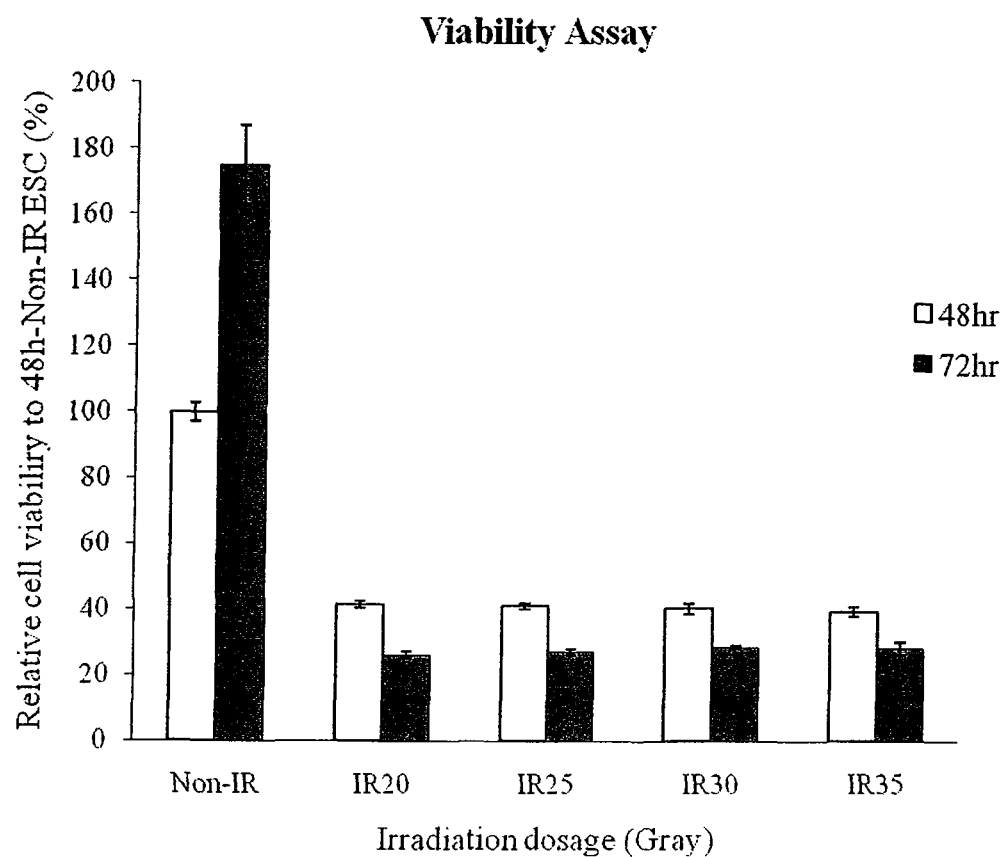

In order to understand why IR-ESC did not stimulate development of teratomas, we investigated if irradiation diminished the proliferation ability of ESC. Both ESC and IR-ESC were assessed for ex vivo proliferation and viability. When exposed to irradiation in culture, ESC proliferation was not detectable at doses of 20 to 35 Gy irradiation (FIG. 7a). ESC survival was reduced ex vivo within 48 hours after doses of greater than 20 Gray (FIG. 7b). FIG. 7a describes proliferation ability of ESC treated with different dosage of irradiation (0,20,25,30,35 Gray) and different duration of treatment (48, 72, 96 hr) as determined by 96-well Hoech- dye-based assay. Cell number were normalized to cell number of ESC received no irradiation after 48 hr. All values are presented as mean±SD. FIG. 7b describes cell viability of ESC treated with different dosage of irradiation (0,20,25, 30,35 Gray) and different duration of treatment (48, 72 hr) is determined by 96-well viability assay as described. Cell number were normalized to cell number of ESC received no irradiation after 48 hr. All values are presented as mean±SD.

Figure 8A:
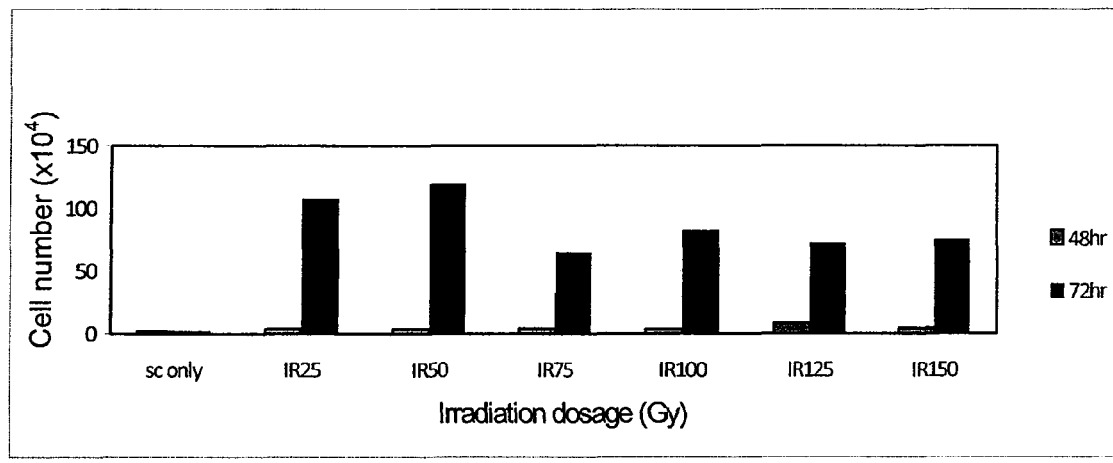
FIG. 8a and FIG. 8b compares survival of irradiated ESC (IR-ESC) co-cultured cardiomyocytes and non-co-cultured cardiomyocytes.
Figure 8B:
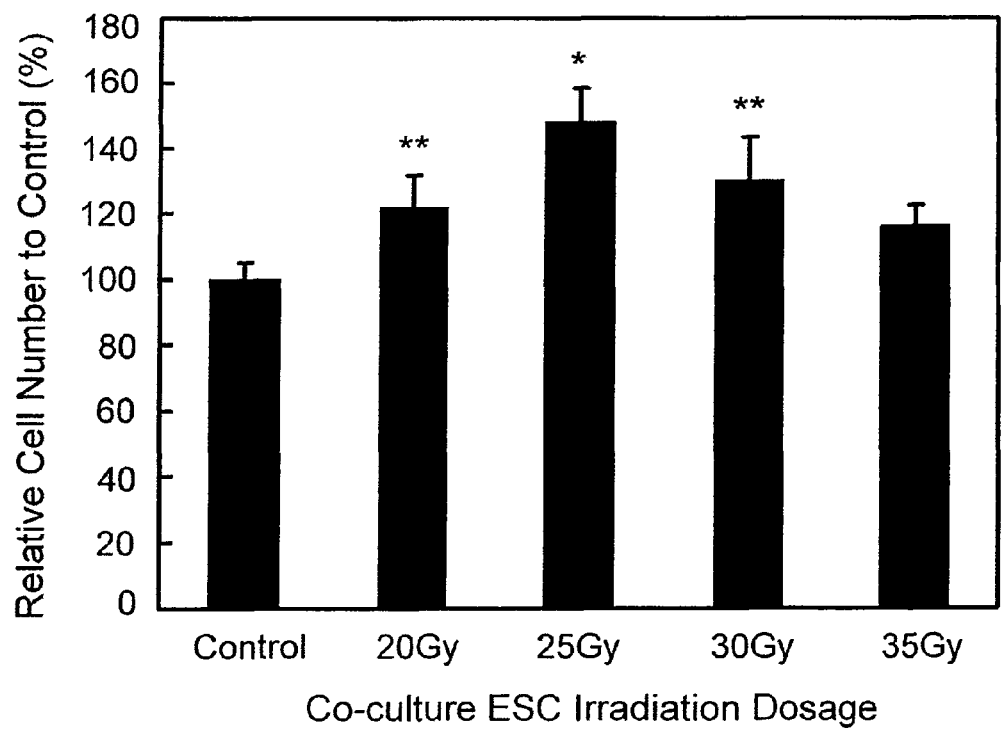

Mitotically inactivated ESC provide a potent in vitro feeder cell proliferation and survival effect on primary cell cultures. Since IR-ESC is unable to proliferate after irradiation, IR-ESC may secrete or contain certain signaling molecules to stimulate proliferation of nearby splencytes and cardiomyocytes. To test this hypothesis, we evaluated if IR-ESC can serve as a potential feeder cells for primary cultures of splenocytes and cardiomyocytes. When freshly isolated mouse splenocytes were co-cultured with IR-ESC, splenocyte numbers proliferated exponentially compared to non-co-cultured cells even when IR-ESC were pre-treated with up to 150 Gray irradiation (FIG. 8a). In FIG. 8a, IR-ESC=irradiated embryonic stem cells, IR=irradiated, IR25=irradiated with 25 Gray, IR50=irradiated with 50 Gray, IR75 =irradiated with 75 Gray, IR100=irradiated with 100 Gray, IR125=irradiated with 125 Gray, IR150=irradiated with 150 Gray, Sc=splenocytes Primary mouse cardiomyocytes isolated from adult hearts were co-cultured in transwells with IR-ESC without direct contact for 48 hours. IR-ESC co-cultured cardiomyocyte survival was significantly higher compared to non-co-cultured cardiomyocytes (FIG. 8b). FIG. 8b describes increase of cardiomyocytes survival by co-culture with IR-ESC. Primary adult mouse cardiomyocytes were co-cultured with IR-ESC without direct contact in condition medium for 48 hours. IR-ESC were treated with different irradiation dosage (0,20,25,30,35 Gray). Cell number of cardiomyocytes was determined by hemacytometer counting. Non-co-cultured cardiomyocytes included as control in this assay. Relative cell number to control were plotted in a bar graph. *P<0.01 v.s. co-culture with 25 Gy irradiated ESC. **P<0.05 v.s. co-culture with 20 and 30 Gy irradiated ESC. All values are presented as mean±S.E.M. Non-irradiated ESC over-grew culture conditions and were thus not evaluated, while we confirmed that IR-ESC can function as an ex vivo feeder-layer for cardiomyocytes enhancing ex vivo survival.

Fluorescence In Situ Hybridization Evaluation for ESC-Derived Cells Within Myocardium.

To determine if injected IR-ESC will survive and remain in recipient mice, male IR-ESC (Y chromosome positive) were injected into female MI mice for myocardial repair. One month after coronary artery ligation, hearts were studied for the remaining Y-chromosome by fluorescent in situ hybridization. The existence of Y chromosome indicating the persistence of surviving donor (male) ESC. The Y chromosome was detectable in less than 0.0025% (1 in 40,000) counted cardiac nuclei. The rare Y-chromosome positive cell occurred in isolated nuclei surrounded by Y chromosome negative nuclei.

In Vivo Cardiomyocyte Proliferation

Figure 9:
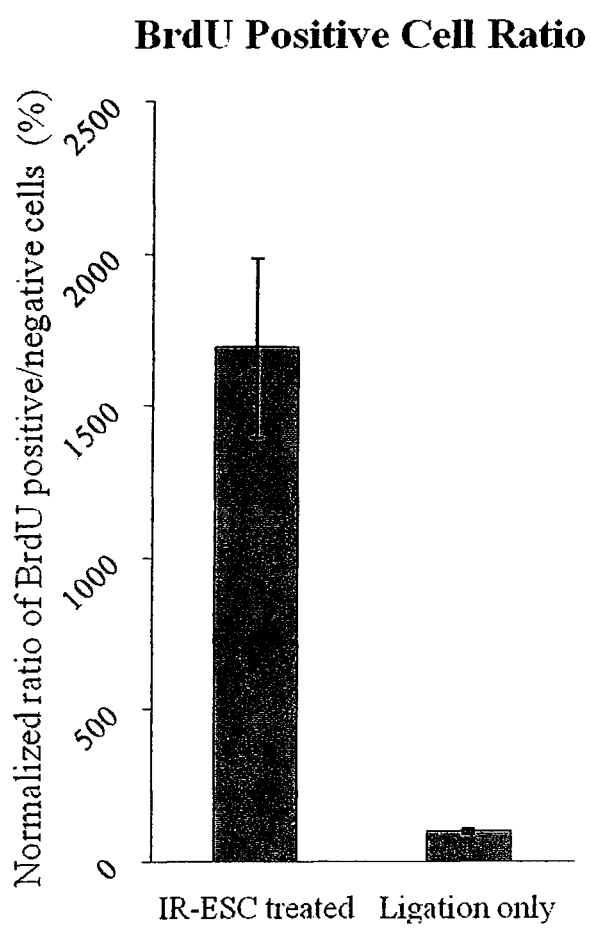
FIG. 9 illustrates IR-ESC simulation on proliferation of cardiomyocytes in vivo.

To determine if IR-ESC promote proliferation of cardiomyocytes in vivo, recipient mice after coronary artery ligation received intraperitoneal daily injections for 5 days of 5-bromo-2-deoyuridine (BrdU), a synthetic nucleoside analog of thymidine incorporated into the DNA of dividing cells. One month after coronary artery ligation, hearts were analyzed by immunohistochemistry for nuclei containing BrdU. Mice treated with IR-ESC demonstrated streaks of BrdU positive cardiomyocytes within the previously ischemic left ventricle but not within the right ventricle or atrium. The percent age of BrdU positive nuclei within the left ventricle was 15.6% (FIG. 4 and photograph 2). Control mice who underwent ischemic myocardial injury without receiving IR-ESC demonstrated a rare and isolated (<0.009%) BrdU positive nucleus (FIG. 9). FIG. 9 describes immunostaining for 5-bromo-2-deoxyuridine (BrdU)-positive cardiomyocytes after 1 month treatment as mentioned in Material & Methods. Number of newly proliferated cardiomyocytes were determined by BrdU-positive cell count. The ratio of BrdU-positive cells to BrdU-negative cell is normalized to ligation only control. All values are presented as mean±SD.

What is claimed is:

1. A method for treating whole body radiation injury in a mammal, the method comprising:
   intravenously injecting the mammal with an effective amount of lethally inactivated mammalian pluripotent stem cells that cannot undergo mitosis, the lethally inactivated mammalian stem cells being of the same species as the mammal undergoing treatment, wherein the effective amount provides the treated mammal with an improved rate of survival after radiation injury.

2. The method of claim 1, wherein the pluripotent stem cells are isolated from embryos, placenta, or amniotic fluid or generated from any tissue or cell line.

3. The method of claim 1, wherein the stem cells have been lethally inactivated with at least one of irradiation, mitomycin C, and phototherapy.

4. A method for treating whole body radiation injury in a mammal, the method comprising:
    treating mammalian pluripotent stem cells in a manner effective to provide lethally inactivated mammalian pluripotent stem cells that cannot undergo mitosis; and
    intravenously injecting the mammal with an effective amount of the lethally inactivated mammalian pluripotent stem cells, the lethally inactivated mammalian pluripotent stem cells being of the same species as the mammal undergoing treatment, wherein the effective amount provides the treated mammal with an improved rate of survival after radiation injury.

5. The method of claim 4, wherein the pluripotent stem cells are isolated from embryos, placenta, or amniotic fluid or generated from any tissue or cell line.

6. The method of claim 4, wherein treating the pluripotent stem cells comprises treating the pluripotent stem cells with at least one of irradiation, mitomycin C, and phototherapy.

* * * * *